United States Patent [19]

Krieg et al.

[11] Patent Number: 4,973,676
[45] Date of Patent: * Nov. 27, 1990

[54] PLASMIDS, GENES AND DNA EXPRESSING A BACILLUS THURINGIENSIS PROTEIN TOXIC TO COLEOPTERA AND BACTERIA TRANSFORMED THEREBY

[75] Inventors: Aloisius Krieg, Darmstadt; Alois Huger, Darmstadt-Eberstadt; Wolfgang Schnetter, Bammental, all of Fed. Rep. of Germany

[73] Assignee: Boehringer Mannheim GmbH, Mannheim, Fed. Rep. of Germany

[*] Notice: The portion of the term of this patent subsequent to Dec. 26, 2006 has been disclaimed.

[21] Appl. No.: 259,161

[22] Filed: Oct. 18, 1988

Related U.S. Application Data

[60] Division of Ser. No. 195,511, May 18, 1988, Pat. No. 4,851,340, which is a division of Ser. No. 27,991, Mar. 13, 1987, Pat. No. 4,766,203, which is a continuation of Ser. No. 681,918, Dec. 14, 1984, abandoned.

[30] Foreign Application Priority Data

Dec. 21, 1983 [DE] Fed. Rep. of Germany ....... 3346138

[51] Int. Cl.$^5$ .................... C07H 19/00; C07H 21/00; C12P 21/00; C12P 19/44
[52] U.S. Cl. .................................. 536/22; 435/69.1; 435/832; 435/320; 435/252.3; 935/23; 935/27; 935/56; 935/74; 536/27
[58] Field of Search ...................... 424/93, 405; 514/2; 530/370, 825; 435/253, 68, 91, 832, 252.5; 935/23, 27, 56, 74; 536/22

[56] References Cited

U.S. PATENT DOCUMENTS 4,766,203  8/1988  Krieg et al. .................... 530/825
4,853,331  8/1989  Herrnstadt et al. ................ 530/350

OTHER PUBLICATIONS

Schnepf et al, "Cloning and Expression of the Bacillus thuringiensis Crystal Protein Gene in Escherichia Coli", Proc. Natl. Acad. Sci., USA, vol. 78, No. 5, pp. 2893-2897, May 1981.

Sekar et al., "Molecular Cloning and Characterization of the Insecticidal Crystal Protein Gene of Bacillus thuringiensis vari tenebriouis", DNAS, vol. 84, pp. 7036-7040, Oct. 1987.

Herrnstadt et al., "Nucleotide Sequence and Deduced Amino Acid Sequence at a Coleopteran-Active Delta--Endotoxin Gene from Bacillus thuringiensis subsp. San Diego", Gene, 57 (1987) 37-46.

Primary Examiner—John Kight
Assistant Examiner—Nathan M. Nutter
Attorney, Agent, or Firm—Felfe & Lynch

[57] ABSTRACT

The invention comprises DNA expressing a Bacillus thuringiensis protein toxic to Coleoptera, as well as the gene which expresses the protein. Also included are plasmids which contain this DNA and non-Bacillus thuringiensis bacterium transformed by the DNA, the plasmid, or the gene.

7 Claims, No Drawings

PLASMIDS, GENES AND DNA EXPRESSING A BACILLUS THURINGIENSIS PROTEIN TOXIC TO COLEOPTERA AND BACTERIA TRANSFORMED THEREBY

This application is a divisional of Ser. No. 195,511, filed May 18, 1988 and now U.S. Pat. No. 4,851,340, which is a divisional of Ser. No. 027,991 filed Mar. 13, 1987, now U.S. Pat. No. 4,766,203 which is a continuation of Ser. No. 681,918, filed Dec. 14, 1984, now abandoned.

The present invention is concerned with a new strain of Bacillus, with obtaining a toxin therefrom and with a composition for combating Coleoptera.

Besides the chemical insecticides, bacterial insecticides have, for many years, been the subject of intensive investigation. In 1915, *Bacillus thuringiensis* (Bt) was described for the first time as the causative agent of flacherie in flour moth larvae. Up to the 1970's, all isolates of Bt belonged to a pathotype which was only effective against larvae of Lepidoptera. This type is called pathotype A. It includes not only *var. thuringiensis* but also *var. kurstaki* and *var. galleriae*, which are also used in practice.

In 1977, Goldberg and Margalit isolated from a sample originating from mosquito breeding sites in the Negev desert a strain which proved to be pathogenic towards larvae of various Nematocera (Diptera) and which was subsequently classified as *Bacillus thuringiensis var. israelenis* (Bti). This type is called pathotype B. In the meantime, this variety has also been used economically.

The advantage of bacterial insecticides is that they act very selectively on definite kinds of pests.

Thus, for example, U.S. Pat. No. 4,166,122 discloses an insecticide which contains as active component the variety *Bacillus thuringiensis var. israelensis* found by Goldberg. It is very clearly shown therein that this bacterial strain is pathogenic against mosquito larvae, whereas other organisms are not influenced.

However, there is still a need for bacterial insecticides which are active against other groups of pests.

Thus, according to the present invention, there is provided a new variety of *Bacillus thuringiensis* which is called *Bacillus thuringiensis var. tenebrionis* (Btt).

We have found that this strain has an insecticidal activity against certain types of beetles (Coleoptera) and especially against Chrysomelides, for example blue alder leaf beetle (*Agelastica alni*), as well as the Colorado beetle (*Leptinotarsa decemlineato*). Therefore, Btt is representative of a new pathotype, which is named pathotype C.

The present invention also provides a bacterial insecticide which, as active material, contains *Bacillus thuringiensis* of pathotype C and especially Btt or an insecticidally-active preparation or toxin obtainable therefrom.

The new variety was isolated from an infected pupa of the yellow meal worm (Tenebrio molitor L., Coleoptera: Tenebrionidae). The pure culture is maintained at 25° to 30° C. on nutrient agar slants. The dry spores were frozen or freeze-dried in order to preserve them. The determination was based on morphological and biochemical characteristics.

On nutrient agar, Btt produces large, coarse, whitish colonies, the cells of which sporulate after 18 to 24 hours. The vegetative cell is flagellated and rod-shaped and measures approximately $1.0 \times 4-8$ μm. It reacts grampositively. The sporangium contains, in addition to the subterminally-lying ellipsoidal spore ($0.8 \times 1.4-1.6$ μm), a parasporal crystal with a flat, plate-like form and usually with the shape of a parallelogram, rhombus or quadrat (about 0.8–1.5 μm edge length).

In the vegetative phase, facultative growth of the Bacillus also takes place anaerobically. On the other hand, the sporulation is strictly aerobic. Excellent growth and sporulation takes place at 25° to 30° C. Autoclaving for 15 minutes at 121° C. (corresponding to 1 bar overpressure) clompletely inactivates the spores and also the toxicity of the crystals. By means of UV irradiation at 254 nm, the spores are inactivated at an appropriate UV-dosage but not the toxic crystals.

The biochemical features of the vegetative cells are as follows: From decomposable carbohydrates, for example glucose, there are formed fermentation acid and acetyl methyl carbinol but no gas. Apart from glucose, mannose and saccharose are decomposed with acidification but not lactose, cellobiose, salicin, arabinose, xylose or mannitol. Aesculin is hydrolysed, as well as starch. The following enzymes can be detected: catalase, nitrate reductase and proteinase, whereas the following enzymes could not be detected: lysine decarboxylase, phenylalanine desaminase, urease and lecithinase.

For production purposes on a laboratory scale, there was used a shake culture. 50 ml. amounts of medium were fermented in 250 ml. Erlenmeyer flasks. The medium used had the following composition: 0.5% yeast extract, 0.5% tryptone, 0.1% glucose and 0.08% monopotassium dihydrogen phosphate in tap water (pH 7.0). The selected fermentation temperature was 25° to 30° C. Subsequent to the sporulation of the culture, which can be monitored microscopically, the biomass was sedimented by centrifugation and washed with water or buffer. The spore-crystal preparation can be lyophilized.

The mode of action of Btt on Coleoptera larvae basically resembles that of pathotype A strains on Lepidotera larvae: feeding ceased within the course of a few hours and mortality occured within a few days, depending upon the dosage. The toxic action depends upon the fact that the midgut epithelium cells are damaged by the toxic crystals dissolved in the gut juice. The damaged gut cells from the basement membrane and from one another and drift into the lumen of the gut. As a result of the breakdown of the gut barrier, bacterial cells penetrate into the hemocoel with the consequence of a fatal septicemia.

The new variety Btt, the prototype of which could be isolated from a dead T. molitor pupa, has been deposited with the German Collection of Microorganism under the number DSM 2803. Serological investigations revealed Btt (strain DSM 2803) as a member of serotype H 8*a*, 8*b*.

The new variety Btt, pathotype C, shows a selective insecticidal action on certain Coleoptera, for example on the blue alder leaf beetle and on the Colorado beetle. The action is much stronger in the case of the larva than in the case of the imago. On the other hand, no effect was observed against larvae of Lepidoptera, for example the flour moth (*Ephestia kühniella*) and the cabbage moth (*Plutella xylostella*) as well as against larvae of Diptera, for example the yellow fever mosquito (*Aedes aegypti*). The following Table summarises results of biotests.

TABLE

Toxic action of Btt on various Coleoptera, Lepidoptera and Diptera

| Species investigated | Dosage used (spore equivalents) | Toxic action |
| --- | --- | --- |
| Blue alder leaf beetle | $10^6/cm^2$ | + |
| Colorado beetle | $10^6/cm^2$ | + |
| Mediterranean flour moth | $2.5 \times 10^8/cm^3$ | − |
| Cabbage moth | $4 \times 10^7/cm^2$ | − |
| Yellow fever mosquito | $5 \times 10^6/cm^3$ | − |

The actual insecticidal principle of *Bacillus thuringiensis* of pathotype C is the parasporal toxic crystal. The crystal moiety can be isolated in that, in sporulated cultures, after lysis of the sporangia the crystals are separated from the cell residues and the spores and purified, for example via density gradients.

Molecular weight determination with Btt by aid of SDS-polyacrylamide gel electrophoresis, using the method of Laemmli (Nature, 227, 680/1970), revealed two main bands at approximately 65,000 D and approximately 70,000 D. Several bands of lesser intensity were found between 20,000 to 40,000 D. The toxin according to the present invention produces antibodies which show no cross reactivity with other toxins of pathotype A or B in an immuno-diffusion-test according to Ouchterlony.

The toxin is coded by a gene which is included in a plasmid. The toxin can also be produced in asporogenic mutants obtained by mutageneses with ethylmethanosulfonat. The ability to produce the toxin can be transmitted by plasmid or gen transfer to other varieties of Bt of other bacterial systems. The insecticidal effect is based on the presence of the plasmid coded toxin.

For use as an insecticide, *Bacillus thuringiensis var. tenebrionis* or an insecticidally-active preparation or toxin obtained therefrom is mixed in known manner with conventional additives (carrier materials, adhesion agents, wetting agents etc.) and converted into a form suitable for use. The insecticide formulated in this manner can be used, for example, in the form of a spray powder, a suspension, as a granulate or the like.

Preferably a purified, sporulated culture is used in form of a suspension with the addition of a wetting agent, for example 0.1% Citowet (BASF). $10^{12}$ to $10^{15}$, preferably $10^{13}$ to $10^{14}$ spores and an equivalent number of toxic crystals per hectacre are usually dispersed. For example in this way potato plants can be protected against Colorado beetles for 2 to 4 weeks. Additional treatments are necessary in order to protect the plants during the whole growth period. No effect against non target organisms, especially against entomophages and honey bees was observed.

What is claimed is:

1. Plasmid containing DNA which expresses a *Bacillus thuringiensis* protein toxin having a molecular weight of from approximately 65 to about 70 kilodaltons which is toxic to Coleoptera.

2. Bacterium transfored by the plasmid of claim 1.

3. Substantially pure gene which expresses a protein toxin of Bacillus thurigiensis which protein toxin has a molecular weight of from approximately 65 to about 70 kilodaltons and which is toxic to Coleoptera and substantially non toxic against Lepidoptera and Diptera.

4. Non-*Bacillus thuringiensis* bacterium which has been transformed by the plasmid of claim 1.

5. Non-*Bacillus thuringiensis* bacterium which has been transformed by the substantially pure gene of claim 3.

6. Substantially pure DNA sequence which expresses a protein toxin of Bacillus thuringiensis having a molecular weight of from approximately 65 to about 70 kilodaltons which is toxic to Coleoptera and substantially non-toxic against Lepidoptera and Diptera.

7. Non-*Bacillus thuringiensis* bacterium which has been transformed by the DNA of claim 6.

* * * * *

UNITED STATES PATENT AND TRADEMARK OFFICE
CERTIFICATE OF CORRECTION

PATENT NO. : 4,973,676
DATED : November 27, 1990
INVENTOR(S) : Aloisius Krieg et al.

It is certified that error appears in the above-identified patent and that said Letters Patent is hereby corrected as shown below:

Title Page, second column: under "Other Publications" the following citations should be added:

-- Sharpe, J. Invert. Path 27: 421-422 (1976).

Bulla et al. "Ultrastructure, Physiology and Biochemistry of Bacillus Thuringiensis in CRC Critical Reviews In Microbiology" (CRC Press, October 1980), pages 147-204. --

Column 4, line 22 (claim 2): change "transfored" to -- transformed --.

Column 4, line 24 (claim 4): change "thurigiensis" to -- thuringiensis --.

Signed and Sealed this

Second Day of June, 1992

*Attest:*

DOUGLAS B. COMER

*Attesting Officer*  Acting Commissioner of Patents and Trademarks

UNITED STATES PATENT AND TRADEMARK OFFICE
CERTIFICATE OF CORRECTION

PATENT NO. : 4,973,676

DATED : November 27, 1990

INVENTOR(S) : Aloisius Krieg et al.

It is certified that error appears in the above-identified patent and that said Letters Patent is hereby corrected as shown below:

Title page: at "Notice" change "December 26,2006" to -- August 23, 2005 --.

Signed and Sealed this

Twentieth Day of October, 1992

Attest:

DOUGLAS B. COMER

*Attesting Officer*  *Acting Commissioner of Patents and Trademarks*